(12) United States Patent
Larson

(10) Patent No.: US 6,935,342 B2
(45) Date of Patent: Aug. 30, 2005

(54) MEDICAL ARM RESTRAINING DEVICE

(76) Inventor: Brent Larson, 36 N. 700 East, Springville, UT (US) 84663

( * ) Notice: Subject to any disclaimer, the term of this patent is extended or adjusted under 35 U.S.C. 154(b) by 93 days.

(21) Appl. No.: 10/117,724

(22) Filed: Apr. 4, 2002

(65) Prior Publication Data

US 2002/0148474 A1 Oct. 17, 2002

Related U.S. Application Data

(60) Provisional application No. 60/283,673, filed on Apr. 13, 2001.

(51) Int. Cl.[7] .............................................. A61B 19/00
(52) U.S. Cl. ....................... 128/869; 128/876; 128/878; 119/770; 297/466; 297/467
(58) Field of Search ................................ 119/770, 769, 119/792; 128/869, 870, 876, 878, 879; 297/464, 466, 467

(56) References Cited

U.S. PATENT DOCUMENTS

| | | | |
|---|---|---|---|
| 1,310,958 A | * | 7/1919 | O'Connor .................. 297/484 |
| 1,636,101 A | | 7/1927 | McLallen |
| 2,425,489 A | | 8/1947 | Peterson |
| 3,324,851 A | | 6/1967 | Posner |
| 4,172,453 A | | 10/1979 | Leckie |
| 4,481,942 A | | 11/1984 | Duncan |
| 4,860,560 A | | 8/1989 | Lundelius |
| 5,012,821 A | | 5/1991 | Tarver |
| 5,016,650 A | | 5/1991 | Marlar |
| 5,664,844 A | | 9/1997 | Greene |
| 6,000,402 A | | 12/1999 | Able |

* cited by examiner

Primary Examiner—Henry Bennett
Assistant Examiner—Camtu Nguyen
(74) Attorney, Agent, or Firm—Clayton, Howarth & Cannon, P.C.

(57) ABSTRACT

An arm holding device. The device includes a waist band, a groin strap fitted with an attachment/release buckle, and arms bands which are slidably attached to the waist band. The attachment/release buckle on the groin strap makes placing and removing the device on the patient a simple process. The slidably attached arm bands give the patient limited movement of their arms, while effectively holding the arms of the patient to prevent the patient from aggravating an injury. The device is made of flexible materials to provide as much comfort as possible for the patient, while still being effective.

39 Claims, 4 Drawing Sheets

MEDICAL ARM RESTRAINING DEVICE

CROSS-REFERENCE TO RELATED APPLICATIONS

This application claims the benefit of U.S. Provisional Application Ser. No. 60/283,673, filed Apr. 13, 2001, entitled MEDICAL ARM HOLDING DEVICE which is hereby incorporated by reference herein in its entirety, including but not limited to those portions that specifically appear hereinafter.

STATEMENT REGARDING FEDERALLY SPONSORED RESEARCH OR DEVELOPMENT

Not Applicable.

BACKGROUND OF THE INVENTION

1. The Field of the Invention

The present invention relates generally to an arm holding device, and more particularly, but not necessarily entirely, to an arm holding device for use during medical procedures.

2. Description of Related Art

Arm holding or restraining devices are used in the medical field to prevent patients or wearers from interfering with medical procedures or to keep patients or wearers from aggravating an injury. Holding of a patient's arms is important to prevent the patient from interfering with the doctor when the patient is under anesthesia or flinches nervously. Holding of patient's arms is also important to prevent the patient from picking at their wounds after surgery or otherwise aggravating their injury, such as for the repair of a cleft palate in the case of a child patient. The use of an arm restraining device in the case of children and mentally impaired patients is particularly important because these persons do not understand the nature of their injuries and the need to not cause further injury by touching the wound. Such patients have a propensity to pick at stitches, pull out IV tubes or otherwise hamper the medical procedure. For ease of reference, it is to be understood that when the term "medical procedure" is used herein, it is also to encompass the recovery period after active medical intervention has ceased.

Although arm holding devices have been available in the art, they all have one or more drawbacks, such as they are difficult to fit on, and remove from, the patient. For example, the device shown in U.S. Pat. No. 4,860,560 is inconvenient to place on or take off from a human and is intended to be used with "violent prisoners" and "mental patients" and is not suitable for use on a patient such as an infant or a child undergoing a medical procedure. Further, the device shown in U.S. Pat. No. 5,664,844 is intended to be used to safely tether a human to a high chair, wheel chair, or to a leash such that the human is protected from dangerous entanglement with the tether structures but the '844 reference teaches away from restraining the arms of the human. The devices shown in U.S. Pat. Nos. 4,481,942 and 6,000,402 merely prevent a joint of a limb, for example the knee of a leg or elbow of an arm, from bending. Some of previously available devices are also ineffective because a struggling child or mentally impaired wearer may sometimes be capable of contorting themselves into a position in which they can still access an injury or surgical repair with their hands, thereby rendering the device ineffective. Some wearers may even be able to escape from some of the previously available devices and cause injury to themselves or others. Moreover, some of the devices which have been previously available are also uncomfortable to wear, particularly for children. Still further, a number of the devices which have been previously available are difficult to clean because they are fabricated from materials which are difficult to clean, such as cloth, or because they include rigid components or metal fasteners, for example, see U.S. Pat. Nos. 1,636,101, 2,425,489, 3,324,851, 4,172,453, 5,012,812, and 5,016,650.

It will thus be appreciated that it would be an advantage over the previously available art to provide a medical arm holding device that is easy to place on and take off of the patient and which allows for limited movement of the patient's arms and which is comfortable to wear and easily cleaned and which remains in the proper place on the patient's body.

BRIEF SUMMARY OF THE INVENTION

In view of the disadvantages and drawbacks present in the relevant art it will be appreciated that the present invention minimizes, and in some aspects eliminates, the above-mentioned failures, and other problems, by utilizing the methods and structural features described herein.

In accordance with one aspect of the present invention, a device for holding at least one arm of a patient is provided. The patient, generally being a human patient undergoing a medical procedure, has a torso and two arms.

A flexible torso strap is provided. The torso strap has a front segment, a back segment, a right segment, and a left segment and is adapted to at least partially encircle the patient's torso. It is preferred that the torso strap completely encircle the patient's torso about the patient's waist but complete encirclement is not required and the torso strap may be positioned in a location other than the patient's waist.

A flexible groin strap, having first and second ends, is disposed to attach its first end to the front segment of the torso strap and its second end connected to the rear segment of the torso strap. A means for selectively connecting and disconnecting the first end of the groin strap to the front segment of the torso strap can be carried out by many different structures with a buckle being preferred.

Preferably associated with the flexible groin strap is a support structure comprises a length of fabric have two ends and having its ends sewn to the front segment of the torso strap and wherein the groin strap couples to the length of fabric approximately equidistant from said first and second ends of the length of fabric. The length of fabric is preferably releasably connected to the groin strap using a buckle.

At least one means for holding one of the patient's arms in proximity to the torso strap is provided such that the amount of movement possible by the arm is restricted, and particularly the patient is prevented from touching a wound on the patient's body, and it is preferred that structures be provided to restrain both arms. The structures which hold the patient's arm are exemplary of a grasping means for releasably grasping at least one of the patient's arms.

The arm holding means preferably comprises a strap, preferably fabricated from fabric, with first and second ends provided with a fastener, such as a hook and loop fastener. A means for slidably coupling the arm holding means to the torso strap, such as an oval ring, such that the arm holding means can move along a limited length about the left segment of the torso strap is preferably provided. The structures which slidably connect to the torso strap are exemplary of a linking means for linking the grasping means to the torso strap such that the grasping means is allowed to move along at least a portion of the right segment such that the movement of the patient's right arm is restricted to movement along said portion of the right segment and the movement of the patient's right arm away from torso strap is limited to a predetermined distance such that the patient cannot use said right arm to interfere with a medical procedure.

It is preferred that the patient's arms are held in proximity to the torso strap and their movement is restricted away from the torso strap to no more than in the range from about one centimeter to about twenty centimeters, but in some cases it will be desirable to hold the arm tight against the torso strap.

Also in accordance with the present invention, a method for restraining at least one arm of a patient is described. The illustrative method of restraining one or both arms of a patient, the patient having a torso and two arms, includes the steps of: Applying or fitting a flexible torso strap to the patient, said torso strap having a front segment, a back segment, a right segment, and a left segment, so that the torso strap at least partially encircles the patient's torso; Applying or fitting a flexible groin strap to the patient. The groin strap preferably has first and second ends with the first end of the groin strap being connected to the front segment of the torso strap and the second end of the groin strap being connected to the rear segment of the torso strap; Connecting at least one of the patient's arms to the torso strap such that the amount of possible movement of the arm is restricted to prevent the patient from touching a selected part of the patient's body.

It is preferred that the step of applying a groin strap to the patient include the steps of providing at least one support strap attached to the front segment of the torso strap and connecting the groin strap to the torso strap by releasably connecting the groin strap to the support strap, the support strap attached to the torso strap such that the rotation of the torso strap around the torso of the patient is restricted. The inclusion of the described support strap or support structure desirably limits movement of the torso strap around the body of the patient so that the front segment of the torso strap remains at the front of the patient's torso.

Furthermore, the step of connecting at least one of the patient's arms to the torso strap includes the step of encircling one of the patient's arms with an arm strap having a hook fastener along one portion and a loop fastener along another portion and joining the hook and loop fasteners together such that the arm strap can slidably move along at least a portion of the torso strap.

The advantages of the invention will be set forth in the description which follows, and in part will be apparent from the description, or may be learned by the practice of the invention without undue experimentation. The advantages of the invention may be realized and obtained by means of the instruments and combinations particularly pointed out in the appended claims.

BRIEF DESCRIPTION OF THE DRAWINGS

The features and advantages of the invention will become apparent from a consideration of the subsequent detailed description presented in connection with the accompanying drawings in which.

DETAILED DESCRIPTION OF THE ILLUSTRATIVE EMBODIMENTS

Figure 1A:
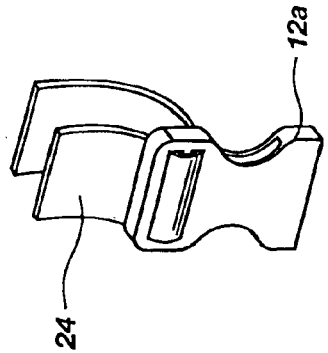
FIG. 1A is a perspective view of a female buckle structure of a releasable connection assembly shown in FIG. 1, with a buckle support strap shown in an exploded, pre-assembled view.

For the purposes of promoting an understanding of the principles in accordance with the present invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Before the present apparatus and methods are disclosed and described, it is to be understood that the present invention is not limited to the particular configurations, steps, and materials disclosed herein as such configurations, steps, and materials may vary somewhat. It is also to be understood that the terminology employed herein is used for the purpose of describing particular embodiments only and is not intended to be limiting since the scope of the present invention will be limited only by the appended claims and equivalents thereof.

All of the publications and other reference materials referred to herein to describe the background of the invention and to provide additional detail regarding its practice are hereby incorporated herein by reference in their entireties. The references discussed herein are provided solely for their disclosure prior to the effective filing date of the present application and nothing herein is to be construed as a suggestion or admission that the inventor is not entitled to antedate such disclosure by virtue of prior invention.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

It will be appreciated that the device of the present invention advantageously provides structures which make the device more effective and easier to use than previously available devices. One such structure which provides clear advantages is a releasable connection assembly which provides that a securing structure, referred to herein as a groin strap, which is positioned between the legs of the patient can be readily connected and disconnected from a structure which encircles the patent's body, referred to herein as a torso strap, which provides that the embodiments of the present invention can be readily fitted on, and removed from, a patient and that the embodiments of the present invention securely fit the patient to prevent undesired movement of the patient's arm or arms. The present invention thus provides a medical arm holding device capable of being easily fitted on, and released from, the patient using a convenient attachment/release structure.

Other structures which provide important advantages are flexible cloth wrist-holding bands which are attached in a manner such that the wrists are able to move along a length of the torso strap and thus allow some limited movement of the patient's arms along the length of the torso strap without compromising the effectiveness of the device in restricting the movement of the patient's arms, for example by preventing the patient from touching his face or head.

Significantly, the illustrative embodiments of the present invention include a single attachment/release structure on a groin strap which allows a medical professional to fit the embodiment of the present invention on the patient, or remove the embodiment from the patient, with little difficulty.

Figure 1B:
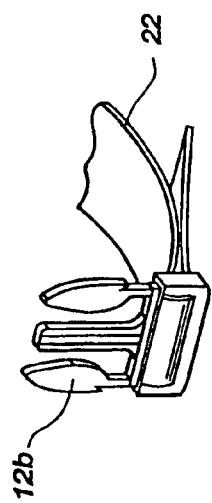
FIG. 1B is a perspective view of a male buckle structure of a releasable connection assembly shown in FIG. 1, with a buckle support strap shown passing through the apertures provided in the buckle structure which function to hold the strap in a desired length.
Figure 1:
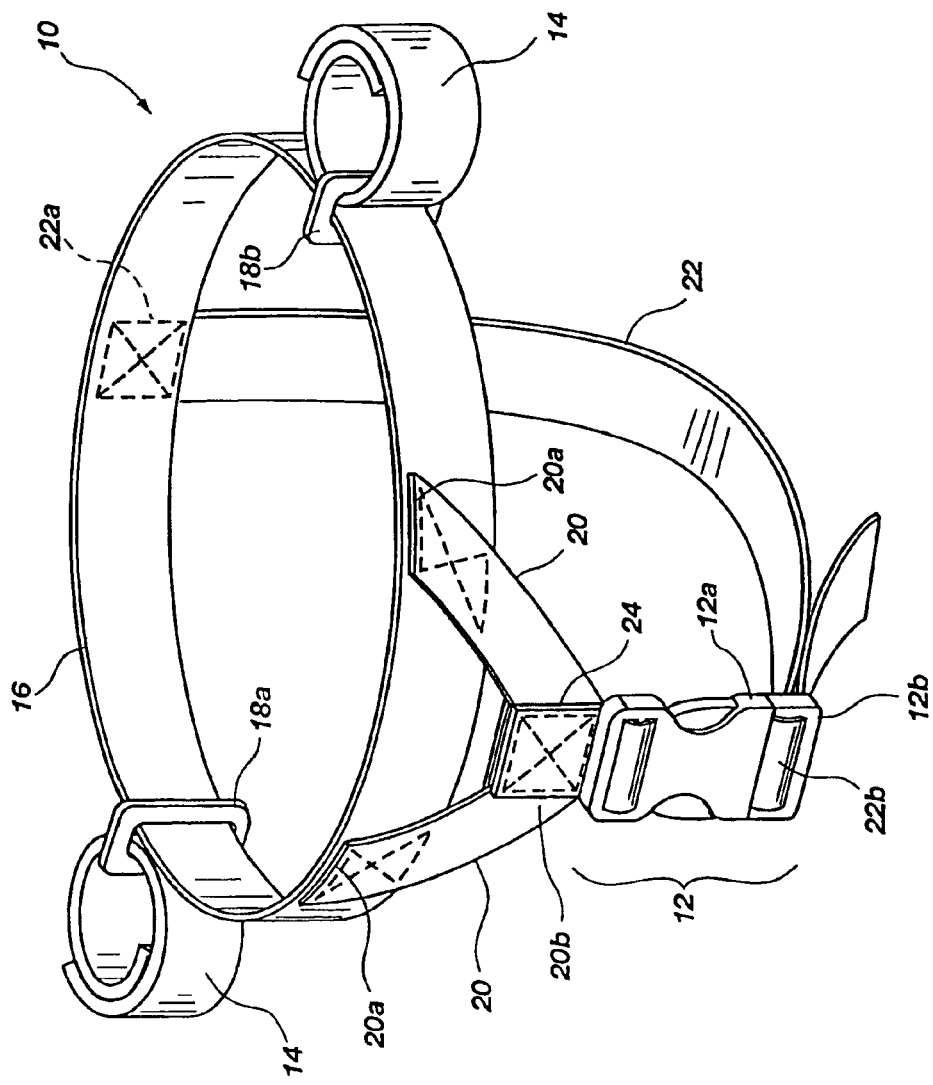
FIG. 1 is a front perspective view of the medical arm holding device with the device positioned as if it were fitted onto a patient.

Referring now to FIG. 1, there is shown a front view of an illustrative embodiment of the medical arm holding device of the present invention, designated generally at 10. The device 10 includes a torso strap 16, a groin strap 22, support straps 20, a buckle support strap 24, a releasable connection assembly buckle (indicated at bracket 12 in FIG. 1), arm bands 14, and arm band attachment structures 18a&b. In the illustrative embodiment, the torso strap 16 is a flexible, endless loop which functions similarly to a belt around the patient's waist or other portion of the patient's torso. It will be appreciated that the torso strap preferably is positioned to encircle the patient's trunk but the torso strap can also be placed on other portions of the patient's body and that in some cases the strap, or its equivalent, need not always completely encircle the patient's body but structures which only partially encircle the patient's body is all that is necessary to accomplish the function of the present invention and is also within the scope of the present invention.

One of the materials from which the torso strap 16, and the other straps of the device 10, can be fabricated is a fabric, either natural and synthetic, but many other types of materials can also be used within the scope of the present invention. The material from which the straps are fabricated should be selected to provide strength and durability, comfort to the patient, and ease of cleaning. For ease of reference, the portions of the torso strap 16 which are illustrated herein will be referenced as a front segment, a back segment, a right segment, and a left segment, as can be readily ascertained by an examination of FIG. 1.

The arm holding device 10 advantageously also includes a groin strap 22, preferably made of fabric, as indicated above, having a first end 22a and a second end 22b. The first end 22a of the groin strap 22 attaches to the rear segment of the torso strap 16, preferably by sewing, but other techniques can be used to join these structures, as well as the other structures of the illustrative embodiment. The opposing second end 22b of the groin strap 22 passes through two apertures provided in a male buckle structure 12b of the releasable connection assembly buckle 12. As shown best in FIG. 1B, the two apertures provided in the male buckle structure 12b are configured so that as the groin strap 22 is pulled through the apertures, creating tension on the groin strap 22, the effective length of the groin strap shortened and is held by the male buckle structure 12b which advantageously assists with fitting the device 10 on a patient, as will be more fully explained shortly.

Also illustrated in FIG. 1 are support straps 20 which each have an upper end 20a and a lower end 20b, and are preferably made of fabric. The upper ends 20a of the support straps 20 attach to the front segment of the torso strap 16, preferably by sewing. The lower ends 20b of the support straps 20 attach to a buckle support strap 24, preferably by sewing. It will also be appreciated that a single length of material can function as supports straps but it is preferred that the illustrated arrangement be used.

The buckle support strap 24 is looped through both apertures provided on the female buckle structure 12a of the releasable connection assembly buckle 12 (as shown best in FIG. 1A) and attaches back to itself and to the lower ends 20b of the support straps 20, preferably by sewing. The releasable connection assembly buckle 12 is preferably selected from those available in the industry and fabricated from a plastic material but many different releasable connection devices, fabricated from many different materials, can be used in accordance with the present invention.

Figure 2:
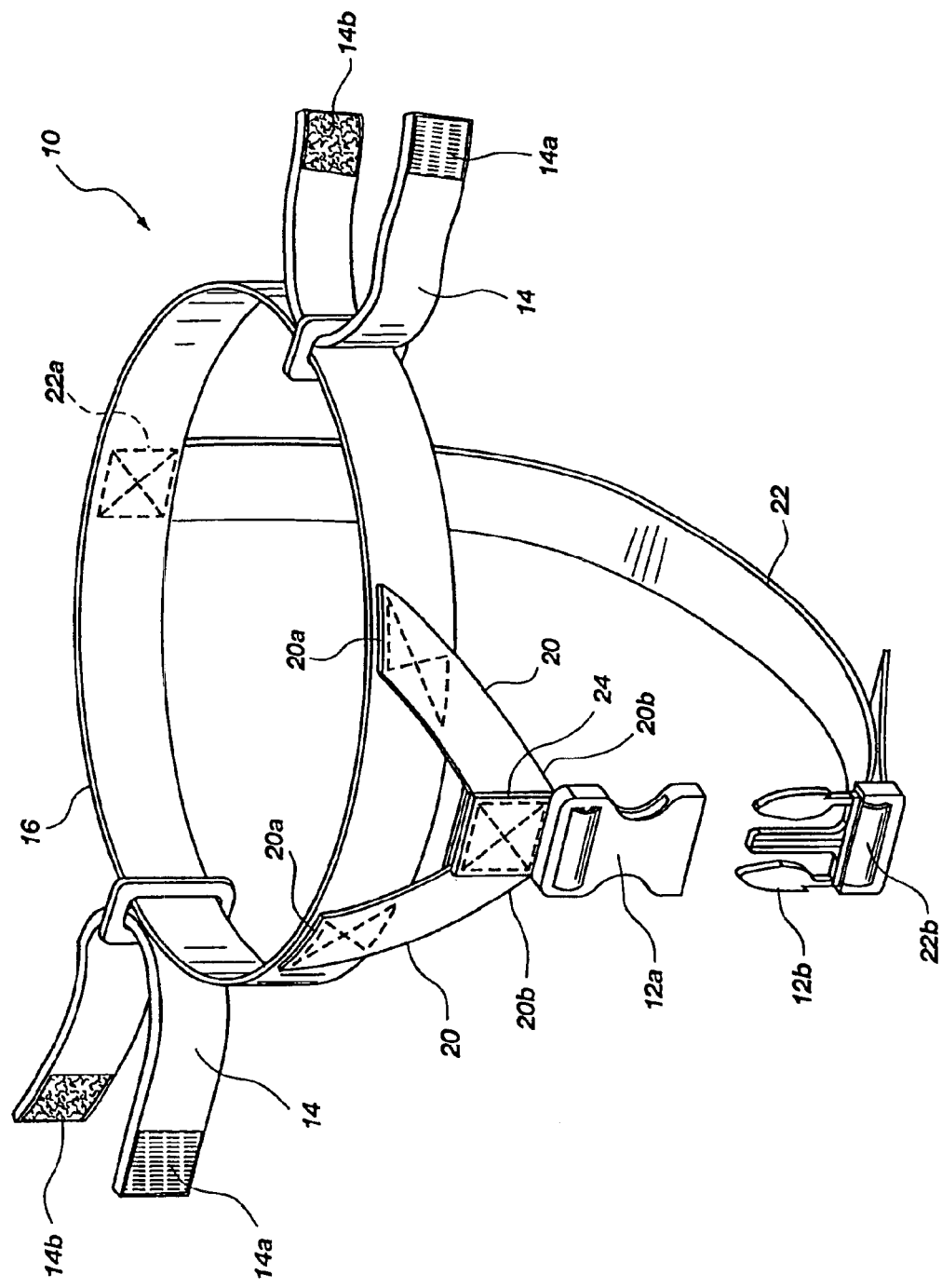
FIG. 2 is a front perspective view of the medical arm holding device with the buckle and arm bands shown in positions removed from the patient.
Figure 3:
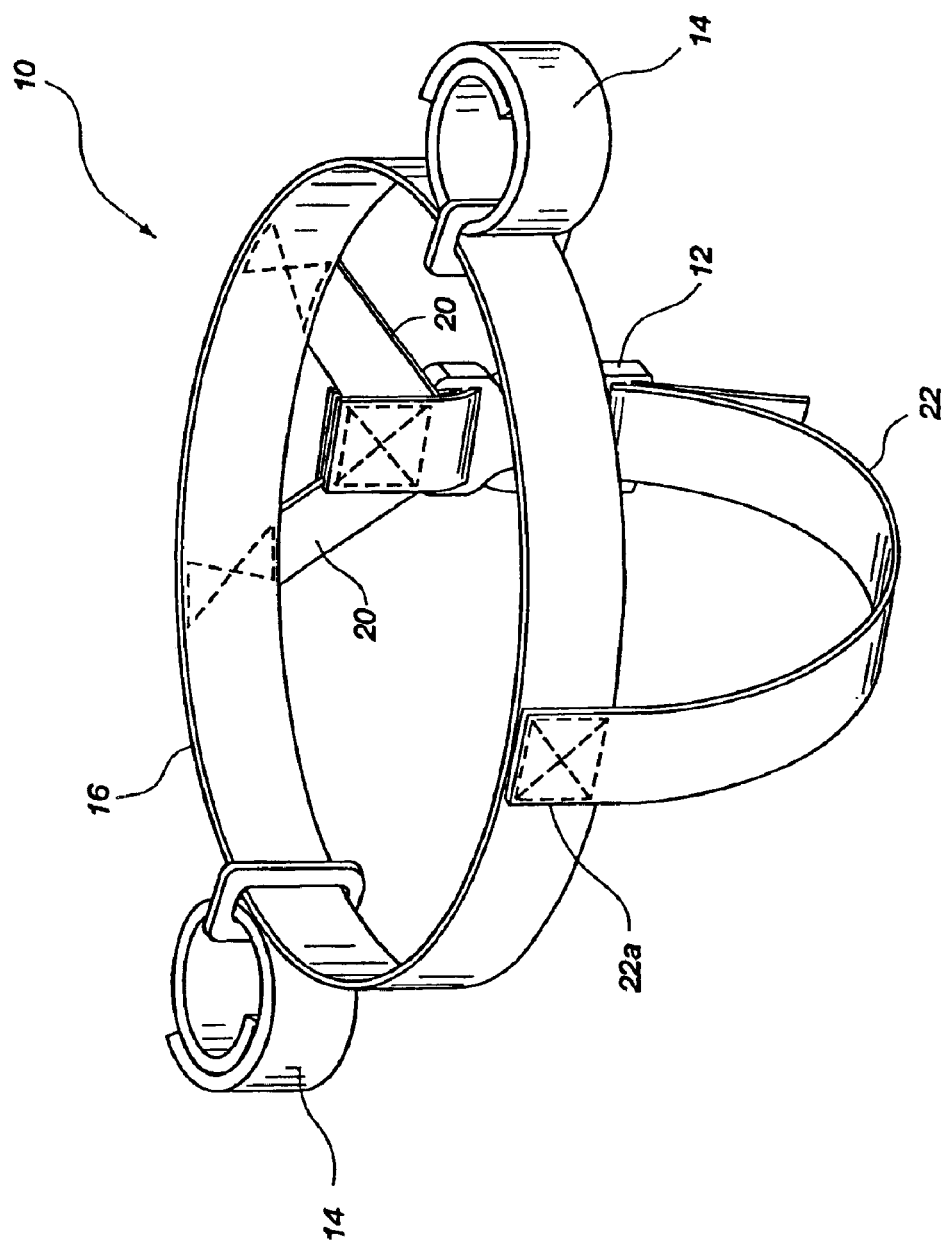
FIG. 3 is a rear perspective view of the medical arm holding device with the releasable connection assembly buckle and arm bands in position as if the device was fitted onto a patient.

It will be appreciated that the arrangement of the support straps 20 illustrated in FIGS. 1, 2 and 3 provides particular advantages. For example, the illustrated arrangement of the support straps 20 provides a better and more secure fit of the device on the patient. The illustrated arrangement prevents the torso strap 16 from being substantially rotated around the body of the patient while the device is being worn and thus the illustrated arrangement provides a more secure fit and better holding of a patient's arm. Moreover, the illustrated arrangement of the support straps 20 and groin strap 22 provides that the device 10 can readily and easily be fitted to a patient. It will be appreciated that the illustrated support straps 20 and the associated structures are one example of a support structure and many different structures can also perform equivalent functions.

It is also within the scope of the present invention to include structures for adjusting the length of the torso strap and for tightening the torso strap about the torso of the patient so that the torso strap can fit many differing sizes of torso. Moreover, in accordance with the present invention, the illustrative embodiment of the present invention is suitable for use with a range of torso sizes found on different patients.

Still referring to FIG. 1, the arm band attachment structures 18a&b are preferably slidably secured to the torso band 16. The illustrative arm band attachment structures 18a&b are ovally-shaped ring structures, preferably made of a plastic, wherein the torso strap 16 passes through the arm band attachment structures 18a&b, such that the attachment pieces can slide along the torso band 16 with the desired amount of friction. Preferably, two arm band attachment pieces 18a&b are secured to the torso strap 16, with the first arm band attachment piece 18a located on the right segment of the torso strap 16 between the groin strap 22 and the support strap 20, and the second arm band attachment structure 18b located on the left portion of the torso strap 16 between the groin strap 22 and the support strap 20. An arm band 14 passes through each of the two arm band attachment structures 18a&b.

The arm bands 14 are preferably fabricated from a material which satisfies the criteria explained above for the other structures of the illustrated embodiment and are shown in a closed configuration in FIG. 1. In the illustrated embodiment, the arm bands 14 can be fabricated from a cloth material, or a cloth covered material, to provide for the comfort of the patient. The arm bands 14, also referred to as arm straps 14, can take many different configurations which will be apparent to those skilled in the pertinent art. The circumference of the arm bands 14 can be readily adjusted to provide an appropriate fit for the patient.

It will be appreciated that the illustrated arm band attachment structures 18a&b and arm bands 14 disclosed herein are merely exemplary of the structures which can function as a means for holding at least one of the patient's arms in proximity to the torso strap and other structures can also carry out this function. It should be appreciated that many different structures, apparatus or systems which perform functions the same as, or equivalent to, the disclosed illustrated arm band attachment structures 18a&b and arm bands 14, are intended to fall within the scope of the present invention, including those structures, apparatus or systems which are presently known, or which may become available in the future.

Furthermore, the arm bands 14, along with the ends 14a and 14b are fitted with a releasable attachment structures, are exemplary of the structures which can function as a grasping means for releasably grasping at least one of the patient's arms and many other structure now know in the art, or which become known in the art, which carry out the same or equivalent functions, also fall within the scope of the grasping means.

Moreover, the arm band attachment structures 18a&b are exemplary of the structures which can function as a linking means for linking the grasping means to the torso strap and many other structure now know in the art, or which become known in the art, which carry out the same or equivalent functions, also fall within the scope of the linking means.

Advantageously, in the illustrative embodiment of the present invention the patient's arm (not represented in the FIG. 1) is held closely to the torso strap. Alternatively, it is within the scope of the present invention to include structures to hold the patient's arms in proximity to the torso strap such that movement of the arm away from the torso strap is restricted to no more than in the range from about one centimeter to about twenty centimeters and can be readily adjusted in increments of one centimeters or other desirable increments. Using the teachings set forth herein, those skilled in the art can readily arrive at other structures which can be used to carry out the desirable function of restricting the movement of the patient's arm. Moreover, as will be readily appreciated from the foregoing, the embodiments of the present invention can be used to restrain just one or both arms of a patient.

It will be appreciated that the arrangement of the support straps 20 illustrated in FIGS. 1, 2 and 3 provides the advantage of limiting the sliding movement of the arm band attachment structures 18a&b along the torso strap 16. The position at which the upper ends 20a of the support straps 20 attach to the torso strap 16 determines the location at which the sliding movement of the arm band attachment structures is stopped.

Referring to FIG. 1A, a view of the female buckle structure 12a of the releasable connection assembly buckle 12, shown in FIG. 1, with the buckle support strap 24 shown in an exploded, pre-assembled view, is provided. The buckle support strap 24 passes through two apertures provided in the female buckle structure 12a, such that the two ends of the buckle support strap 24 form a loop, and the two ends of the buckle support strap 24 are attached to each other and to the lower ends 20b of the support straps 20 as previously described.

It will be appreciated that the support straps 20, the buckle support strap 24, and the releasable connection assembly buckle 12 function as a one example of a connecting means for selectively connecting and disconnecting to the front segment of the torso strap and that many different structures which perform similar functions, both those which are now known and which may become know in the future, all fall within the scope of the connecting means.

Referring now to FIG. 2, the medical arm holding device 10 is shown with the releasable connection assembly buckle 12 and the arm bands 14 in their configurations ready for the device 10 to be fitted onto a patient. The arm bands 14 each have first and second ends 14a and 14b, respectively, wherein said ends 14a and 14b are fitted with a releasable attachment structures, preferably hook and loop fasteners, such as those available under the VELCRO trademark.

In the embodiment illustrated in FIG. 2, the arm band first end 14a is provided with the hook fastener structure and the second end 14b is provided with the loop fastener structure. It will be appreciated that alternative fasteners can be used within the scope of the present invention but the described hook and loop fastener is preferred. In FIG. 2, the male buckle structure 12b of the releasable connection assembly buckle 12 is shown removed from the female buckle structure 12a of the releasable connection assembly buckle 12 with the two buckle structures being mated together to provide a latching engagement when the device 10 is fitted onto a patient.

Reference will now be made to FIG. 3 which provides a rear view of the medical arm holding device 10 with the arm bands 14 and the releasable connection assembly buckle 12 in their fitted positions as if the device 10 were fitted onto a patient. In FIG. 3, the first end 22a of the groin strap 22 is shown attached to the rear segment of the torso band 16, preferably by sewing.

It will be appreciated that the structures disclosed herein are merely exemplary of the embodiments which can be arrived at within the scope of the present invention and it should be appreciated that many different structures, apparatus or systems which perform functions the same as, or equivalent to, those disclosed herein are intended to fall within the scope of the present invention, including those structures, apparatus or systems which are presently known, or which may become available in the future.

In accordance with the features and combinations described above, on illustrative arrangement of the medical arm holding device 10 includes:

(a) a flexible torso strap 16 which functions as a belt;

(b) a groin strap 22 which connects to the rear portion of the torso strap 16 and to two support straps 20, wherein the support straps attach to the front segment of the torso strap 16;

(c) a releasable connection assembly buckle 12 so as to join the groin strap 22 to the structures of the front segment of the torso strap; and (d) flexible arm bands 14, wherein said arm bands 14 slidably attach to the torso strap 16 with the arm band attachment structures 18a&b.

In accordance with the features and combinations described above, an illustrative method of placing the device 10 on a patient includes the steps of:

(a) placing both legs of the patient through the torso strap 16 so the torso strap 16 fits around the patient's waist, with the support straps 20 and the female buckle structure 12a of the releasable connection assembly buckle 12 being positioned on the front side of the patient;

(b) passing the groin strap 22 and the male buckle structure 12b between the patient's legs towards the front side of the patient;

(c) sliding the male buckle structure 12b of the releasable connection assembly buckle 12 into the female buckle structure 12a of the releasable connection assembly buckle 12 and latching the structures together;

(d) adjusting the effective length of the groin strap 22 by pulling a length of the groin strap 22 through the apertures of the male buckle structure 12b (see FIG. 1B) to effectively shorten the length of the groin strap 22 and tightening the device 10 on the patient in a snug fashion; and (e) placing the arm bands 14 around the wrists of the patient and fastening together the first end 14a and the second end 14b of the arm band 14 to snugly fit the arms of the patient.

Figure 4:
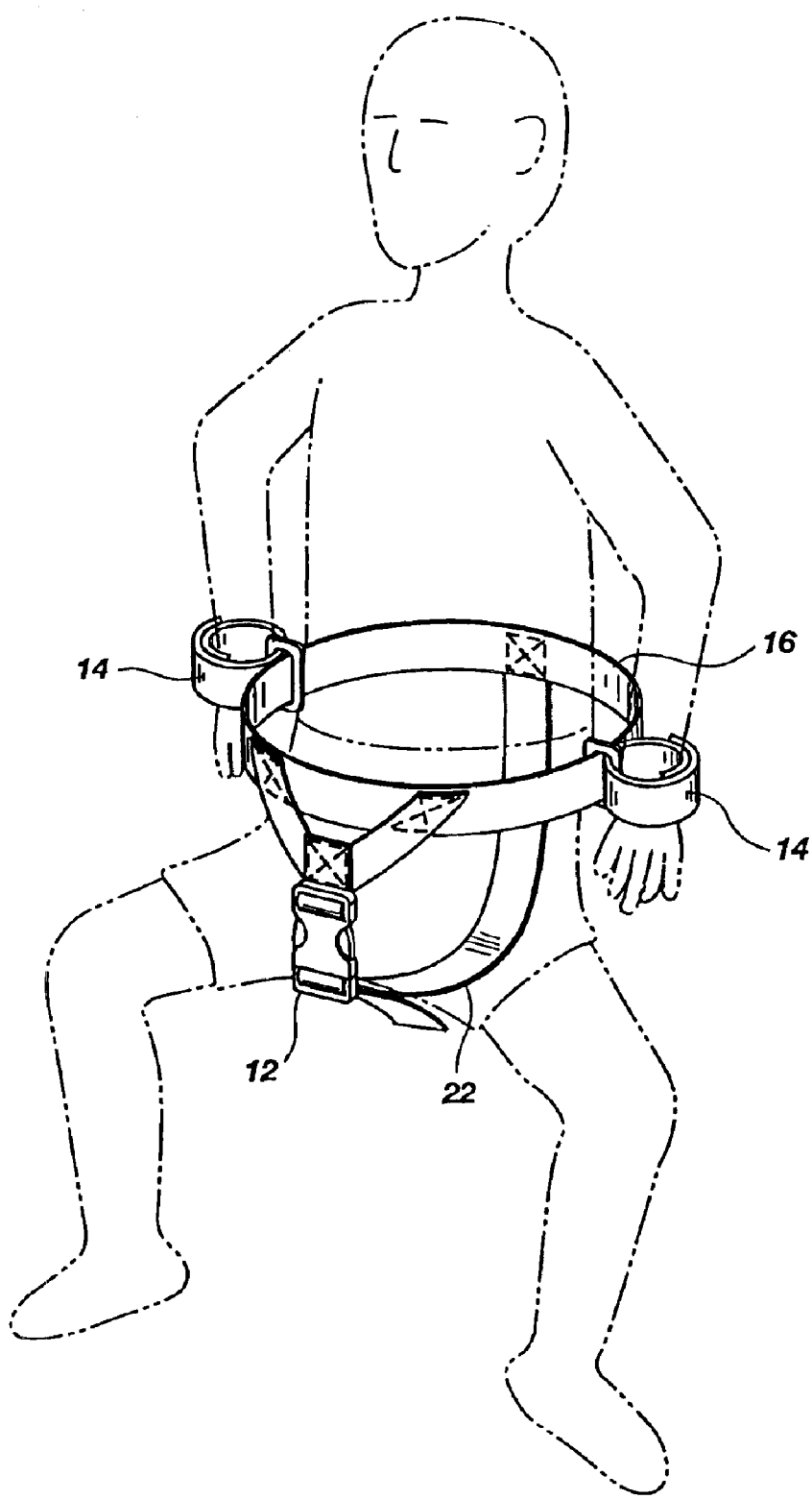
FIG. 4 is a perspective view of the medical arm holding device fitted onto a patient.

Reference will next be made to FIG. 4 which is a perspective view of the device 10 fitted onto a patient. The patient represented in FIG. 4 is intended to represent a child but it will be appreciated that the present invention provides advantages when used with patients of all ages and sizes. Moreover, it is to be understood that the term "medical," as used herein, is intended to encompass any procedure, technique, treatment, or program which is intended to affect or change any part of a patient's body regardless of whether a particular procedure, technique, treatment, or program is traditionally included within the scope of the term "medical."

In view of the foregoing description, it will be appreciated that the incorporation of the groin strap 22 and the releasable connection assembly buckle 12 on the groin strap 22, in combination with the other elements of the device 10, provides distinct advantages. The groin strap 22 prevents the patient from moving or manipulating the device 10 in an upward direction on the patient's body. None of the previously available art shows effective use of a structure which performs functions the same as, or equivalent to, the groin strap described herein. For example, the inclusion of at releasable connection assembly buckle 12 to the groin strap 22 makes the fitting and removal of the device 10 much simpler, easier, and faster than previously possible.

Importantly, the use of the arm band attachment structures 18a&b to slidably attach the arm bands 14 to the torso strap 16 provides advantages not heretofore available in a medical arm holding device. Use of the described arm band attachment structures 18a&b allows the patient to have limited movement of their arms along the length of the torso strap 16, yet prevents the patient from being able to touch, for example, his face and further aggravate their injury or interfere with a medical procedure.

In view of the foregoing, it will be appreciated that the present invention provides a medical arm holding device that is convenient for a care giver to fit onto and remove from a patient and which allows for limited movement of the patient's arms. Furthermore, the present invention provides a medical arm holding device that is comfortable for a patient to wear and easily cleaned and which provides a medical arm holding device which is secure on the patient and which does not slide out of position on the patient's body.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A device for holding at least one arm of a patient, the patient having a torso and two arms, the device comprising:
   a flexible torso strap, said torso strap having a front segment, a back segment, a right segment, and a left segment and being adapted to at least partially encircle the patient's torso;
   a flexible groin strap having first and second ends, wherein said first end is disposed to attach to the front segment of the torso strap and wherein the second end is connected to the rear segment of the torso strap;
   means for selectively connecting and disconnecting the first end of the groin strap to the front segment of the torso strap; and
   at least one means for holding at least one of the patient's arms in proximity to the torso strap such that the amount of movement possible by the arm is restricted.

2. The device for holding an arm of a patient as defined in claim 1, further comprising means for adjusting the length of the torso strap.

3. The device for holding an arm of a patient as defined in claim 1, further comprising means for tightening the torso strap about the torso of the patient.

4. The device for holding an arm of a patient as defined in claim 1, wherein the means for holding at least one of the patient's arms in proximity to the torso strap restricts the movement of the arm away from the torso strap to no more than in the range from about one centimeter to about twenty centimeters.

5. The device for holding an arm of a patient as defined in claim 1, wherein the means for holding at least one of the patient's arms in proximity to the torso strap restricts the movement of the arm away from the torso strap to no more than in the range from about one centimeter to about twenty centimeters and allows movement of the patient's arm along the length of the left segment of the torso strap.

6. The device for holding an arm of a patient as defined in claim 1, wherein said first end of the groin strap is coupled to a connecting means for selectively connecting and disconnecting to the front segment of the torso strap.

7. The device for holding an arm of a patient as defined in claim 6, wherein the connecting means comprises a length of fabric having a first end and a second end, wherein said first and second ends of said connecting means are sewn to the front segment of the torso belt and wherein the groin strap couples to the connecting means approximately equidistant from said first and second ends of said connecting means.

8. The device for holding an arm of a patient as defined in claim 7, wherein the groin strap couples to the connecting means with a buckle.

9. The device for holding an arm of a patient as defined in claim 7, wherein the arm holding means comprises a strap, with first and second ends.

10. The device for holding an arm of a patient as defined in claim 9, wherein said strap comprises a fabric and fastening means for fastening the first and second ends.

11. The device for holding an arm of a patient as defined in claim 10, wherein said fastening means comprises a hook and loop fastener.

12. The device for holding an arm of a patient as defined in claim 11, further comprising means for slidably coupling the arm holding means to the torso strap such that the arm holding means can move along a limited length about the left segment of the torso strap.

13. The device for holding an arm of a patient as defined in claim 12, the means for slidably coupling the arm holding means to the torso strap comprises a rigid oval ring.

14. The device for holding an arm of a patient as defined in claim 12, wherein said means for coupling comprises a buckle.

15. A method for restraining at least one arm of a patient, the patient having a torso and two arms, the method comprising the steps of:

applying a flexible torso strap to the patient, said torso strap having a front segment, a back segment, a right segment, and a left segment, so that the torso strap at least partially encircles the patient's torso;

applying a flexible groin strap to the patient, said groin strap having first and second ends, so that the first end of the groin strap is connected to the front segment of the torso strap and so that the second end of the groin strap is connected to the rear segment of the torso strap; and connecting at least one of the patient's arms to the torso strap such that the amount of movement possible by the arm is restricted.

16. The method for restraining an arm of a patient as defined in claim 15, wherein the step of applying a flexible torso strap comprises the step of adjusting the length of the torso strap;

wherein the step of connecting at least one of the patient's arms to the torso strap comprises the step of restricting the movement of the arm away from the torso strap to no more than in the range from about one centimeter to about twenty centimeters and allows movement of the patient's arm along the length of a segment of the torso strap.

17. The device for holding an arm of a patient as defined in claim 15, wherein the step of applying a flexible groin strap to the patient comprises the steps of:

providing at least one support strap attached to the front segment of the torso strap; and connecting the groin strap to the torso strap by releasably connecting the groin strap to the support strap, the support strap attached to the torso strap such that the rotation of the torso strap around the torso of the patient is restricted.

18. The device for holding an arm of a patient as defined in claim 17, wherein the step of providing at least one support strap attached to the front segment of the torso strap comprises the step of sewing the ends of the support strap to the front segment of the torso strap and wherein the step of connecting the groin strap to the torso strap comprises the step of mating the groin strap using a connector at a position on the support strap about equidistant from said ends of the support strap.

19. The method for restraining an arm of a patient as defined in claim 15, wherein the step of connecting at least one of the patient's arms to the torso strap comprises the step of encircling one of the patient's arms with an arm strap having a hook fastener along one portion and a loop fastener along another portion and joining the hook and loop fasteners together such that the arm strap can slidably move along at least a portion of the torso strap.

20. A device for holding at least one arm of a patient, the patient having a torso and two arms, the device comprising:

a flexible torso strap, said torso strap having a front segment, a back segment, a right segment, and a left segment and being adapted to at least partially encircle the patient's torso;

a strap structure configured to limit the movement of the torso strap upward on the patient's torso and limit the movement of the torso strap circumferentially about the patient's torso; and grasping means for releasably grasping at least one of the patient's arms; and linking means for linking the grasping means to the torso strap such that the grasping means is allowed to move along at least a portion of the right segment such that the movement of the patient's right arm is restricted to movement along said portion of the right segment and the movement of the patient's right arm away from torso strap is limited to a predetermined distance such that the patient cannot use said right arm to interfere with a medical procedure.

21. The device for holding an arm of a patient as defined in claim 20, wherein the linking means comprises a ringed structure circumscribing said torso strap.

22. The device for holding an arm of a patient as defined in claim 21, wherein the grasping means comprises a flexible strap, the flexible strap having first and second ends.

23. The device for holding an arm of a patient as defined in claim 22, wherein the flexible strap passes through the ringed structure.

24. The device for holding an arm of a patient as defined in claim 22, comprising a fastener provided on each of the first and second ends of the flexible strap.

25. The device for holding an arm of a patient as defined in claim 24, wherein the fastener comprises one component of a hook and loop fastener.

26. The device for holding an arm of a patient as defined in claim 22, wherein the strap structure configured to limit the movement of the torso strap comprises:

a flexible groin strap having first and second ends, wherein said first end is disposed to attach to the front segment of the torso strap and wherein the second end is connected to the rear segment of the torso strap;

a support strap structure interposed between the first end of the groin strap and the torso strap, the support strap structure having two ends, each end being connected to the front segment of the torso strap at spaced apart locations and the support strap structure having an approximate midpoint; and a releasable connector for joining the first end of the groin strap to the midpoint of the support strap structure.

27. A method for restraining an arm of a patient, the patient having a waist, two legs, a torso and a head, the method comprising the steps of:

placing both legs of the patient through a torso strap so the torso strap fits about the patient's waist;

positioning two support straps located on a front segment of the torso strap in the patient's groin;

passing a groin strap between the patient's legs towards the front side of the patient;

encircling at least one arm of the patient with an arm strap, the arm strap being slidably connected to the torso strap such that the some movement of the patient's arm is allowed but movement of the patient's arm is restricted a predetermined distance from a location on the torso strap;

releasably connecting the groin strap to the support straps; and adjusting the effective length of the groin strap such that rotational movement of the torso strap around the patient's torso is restricted via interference with the patient's legs and movement of the torso strap toward the patient's head is restricted and movement of the patent's arm is desirably restricted and such that no further adjustments of the device is necessary to maintain a secure fit on the patient.

28. A method for restraining an arm of a patient, the patient having two legs and a torso and a head, the method comprising the steps of:

selectively placing both legs of the patient or the head of the patient through a torso strap so the torso strap fits about the patient's waist;

positioning a support structure located on a front segment of the torso strap in the patient's groin;

passing a groin strap between the patient's legs towards the front side of the patient;

releasably connecting the groin strap to the support structure;

adjusting the effective length of the groin strap such that rotational movement of the torso strap around the patient's torso is restricted via interference with the patient's legs and movement of the torso strap toward the patient's head is restricted; and encircling at least one arm of the patient with an arm strap, the arm strap being slidably connected to the torso strap such that the some movement of the patient's arm is allowed but movement of the patient's arm is restricted a predetermined distance from a location on the torso strap.

29. A method for restraining an arm of a patient as defined in claim 28, wherein the step of placing both legs of the patient through a torso strap comprises the step of placing both legs of the patient through a flexible fabric torso strap in a position about the patient's waist.

30. A method for restraining an arm of a patient as defined in claim 28, wherein the step of releasably connecting the groin strap to the support structure comprises the step of inserting a first buckle member into a second buckle member.

31. A method for restraining an arm of a patient as defined in claim 30, wherein the step of adjusting the effective length of the groin strap comprises the step of pulling the groin strap through an aperture in the first buckle member.

32. A method for restraining an arm of a patient as defined in claim 28, wherein the step of encircling at least one arm of the patient with an arm strap comprises the step of attaching a first end of the arm strap with the second end of the arm strap using a hook and loop fastener.

33. A method for restraining an arm of a patient as defined in claim 28, wherein the step of encircling at least one arm of the patient with an arm strap comprises the step of securing the arm strap to the torso strap using a ring structure with the torso strap passing through the ring structure and the arm strap being connected to the ring structure.

34. A device for holding the arms of a patient, the patient having a torso, a groin, a first leg, a second leg, a left arm and a right arm, the device comprising:

a torso strap, said torso strap having a front segment, a back segment, a right segment, and a left segment, the torso strap fabricated from a flexible fabric and configured to encircle the patient's torso at about the patient's waist;

a support strap structure positioned at the front segment of the torso strap, the support strap structure comprising at least a first support member and a second support member, the two support members being spaced apart and the support strap structure including a first connector, the support strap structure positioned at the front segment of the torso strap above the groin of the patient;

a groin strap having front and rear ends, the rear end of the groin strap being connected to the rear segment of the torso strap and the front end of the groin strap having a second connector which is releasably received by the first connector so that the groin strap passes between the legs of the patient, the first support member and the second support member being held in a partially spaced apart relationship such that the first support member and the second support member restrict rotational movement of the torso strap around the patient's torso via interference with the first leg and the second leg of the patient;

a first arm holding strap, the first arm holding strap comprising first and second ends, each of the first and second ends being provided with a releasable fastener which can be fastened about the left arm of the patient;

means for slidably coupling the first arm holding strap to the torso strap such that the arm holding strap can move about a portion of the left segment of the torso strap;

a second arm holding strap, the second arm holding strap comprising first and second ends, each of the first and second ends being provided with a releasable fastener which can be fastened about the right arm of the patient; and, means for slidably coupling the second arm holding strap to the torso strap such that the arm holding strap can move about a portion of the right segment of the torso strap whereby the movement of the movement of the patient's left and right arms arm is restricted to no more than a predetermined amount.

35. The device for holding an arm of a patient as defined in claim 34, wherein the releasable fastener comprises a hook and loop fastener.

36. The device for holding an arm of a patient as defined in claim 34, wherein the means for slidably coupling comprises a ring structure encircling the torso strap.

37. A device for holding at least one arm of a patient, the patient having a torso and two arms, the device comprising:

a flexible torso strap, said torso strap having a front segment, a back segment, a right segment, and a left segment and being adapted to at least partially encircle the patient's torso;

a flexible groin strap having first and second ends, wherein said first end is disposed to attach to the front segment of the torso strap and wherein the second end is connected to the rear segment of the torso strap;

means for selectively connecting and disconnecting the first end of the groin strap to the front segment of the torso strap;

at least one means for holding at least one of the patient's arms in proximity to the torso strap such that the amount of movement possible by the arm is restricted;

means for adjusting the length of the torso strap;

means for tightening the torso strap about the torso of the patient;

wherein the means for holding at least one of the patient's arms in proximity to the torso strap restricts the movement of the arm away from the torso strap to no more than in the range from about one centimeter to about twenty centimeters and allows movement of the patient's arm along the length of the left segment of the torso strap;

wherein said first end of the groin strap is coupled to a connecting means for selectively connecting and disconnecting to the front segment of the torso strap;

wherein the connecting means comprises a length of fabric having a first end and a second end, wherein said first and second ends of said connecting means are sewn to the front segment of the torso belt and wherein the groin strap couples to the connecting means approximately equidistant from said first and second ends of said connecting means;

wherein the groin strap couples to the connecting means with a buckle;

wherein the arm holding means comprises a strap, with first and second ends;

wherein said strap comprises a fabric and fastening means for fastening the first and second ends;

wherein said fastening means comprises a hook and loop fastener;

further comprising means for slidably coupling the arm holding means to the torso strap such that the arm holding means can move along a limited length about the left segment of the torso strap.

38. The device for holding an arm of a patient as defined in claim 37, the means for slidably coupling the arm holding means to the torso strap comprises a rigid oval ring.

39. The device for holding an arm of a patient as defined in claim 37, wherein said means for coupling comprises a buckle.

* * * * *